United States Patent [19]

Hayes et al.

[11] 4,028,223

[45] * June 7, 1977

[54] GUARD BEDS IN HYDROCARBON CONVERSION WITH AN ACIDIC MULTIMETALLIC CATALYTIC COMPOSITE

[75] Inventors: John C. Hayes, Palatine; Ernest L. Pollitzer, Skokie, both of Ill.

[73] Assignee: UOP Inc., Des Plaines, Ill.

[ * ] Notice: The portion of the term of this patent subsequent to June 1, 1993, has been disclaimed.

[22] Filed: Aug. 11, 1975

[21] Appl. No.: 603,839

Related U.S. Application Data

[63] Continuation-in-part of Ser. No. 522,209, Nov. 8, 1974, Pat. No. 3,960,710.

[52] U.S. Cl. .............................. 208/91; 208/139; 208/111; 260/683.68
[51] Int. Cl.$^2$ ........................................ C10G 35/08
[58] Field of Search ................ 208/138, 139, 111; 260/683.3, 683.68; 252/441

[56] References Cited

UNITED STATES PATENTS

| | | | |
|---|---|---|---|
| 2,911,357 | 11/1959 | Myers et al. | 208/138 |
| 3,063,933 | 11/1962 | Meiners | 208/91 |
| 3,189,539 | 6/1965 | Sieg | 208/91 |
| 3,576,766 | 4/1971 | Ransch | 260/683.3 |
| 3,644,198 | 2/1972 | Wilhelm | 252/460 |
| 3,775,300 | 11/1973 | Hayes | 208/139 |
| 3,830,727 | 8/1974 | Klaksdahl | 208/139 |
| 3,844,938 | 10/1974 | Wilhelm | 208/139 |
| 3,847,794 | 11/1974 | Ransch | 208/139 |
| 3,881,696 | 5/1975 | Lepeytre et al. | 252/466 B |

*Primary Examiner*—Delbert E. Gantz
*Assistant Examiner*—James W. Hellwege
*Attorney, Agent, or Firm*—James R. Hoatson, Jr.; Thomas K. McBride; William H. Page, II

[57] ABSTRACT

Hydrocarbons are converted by contacting a hydrocarbon charge stock and a hydrogen stream at hydrocarbon conversion conditions, in a reaction zone maintained in a substantially sulfur- and water-free condition by the use of at least one guard bed, with an acidic multimetallic catalytic composite comprising a combination of catalytically effective amounts of a platinum group component, a tin component, a cobalt component, and a halogen component with a porous carrier material. The platinum group component, tin component, cobalt component, and halogen component are present in the multimetallic catalyst in amounts respectively, calculated on an elemental basis, corresponding to about 0.01 to about 2 wt. % platinum group metal, about 0.01 to about 5 wt. % tin, about 0.5 to about 5 wt. % cobalt, and about 0.1 to about 3.5 wt. % halogen. Moreover, these metallic components are uniformly dispersed throughout the porous carrier material in carefully controlled oxidation states such that substantially all of the platinum group metal is present therein in the elemental metallic state, substantially all of the catalytically available cobalt component is present in the elemental metallic state or in a state which is reducible to the elemental metallic state under hydrocarbon conversion conditions or in a mixture of these states, while substantially all of the tin is present therein an oxidation state above that of the elemental metal. A specific example of the type of hydrocarbon conversion process disclosed is a process for the catalytic reforming of a low-octane gasoline fraction wherein the gasoline fraction and a hydrogen stream are contacted under a substantially sulfur- and water-free condition with the acidic multimetallic catalyst disclosed herein at reforming conditions. The sulfur- and water-selective guard bed can be used exclusively on the hydrocarbon charge stock when the hydrogen stream is autogenously produced or it can be used to treat a mixture of the hydrocarbon charge stock and the hydrogen stream. In another mode of operation, separate guard beds can be used on the input hydrocarbon charge stock and on the input hydrogen stream.

18 Claims, No Drawings

GUARD BEDS IN HYDROCARBON CONVERSION WITH AN ACIDIC MULTIMETALLIC CATALYTIC COMPOSITE

CROSS-REFERENCES TO RELATED APPLICATIONS

This application is a continuation-in-part of our prior copending application Ser. No. 522,209 filed Nov. 8, 1974 now U.S. Pat. No. 3,960,710, issued June 1, 1975. The teachings of this prior application are specifically incorporated herein by reference.

The subject of the present invention is an improved process for hydrocarbon conversion with a novel acidic multimetallic catalytic composite wherein at least one sulfur- and water-selective guard bed is used to establish and maintain the reaction environment of the catalytic composite in a substantially sulfur-free and water-free condition, thereby enabling substantially improved catalytic performance. More precisely, the present invention involves a hydrocarbon conversion process which uses a combination of a novel dual-function acidic multimetallic catalytic composite with positive reaction environment control of sulfur and water contaminants to enable substantial improvements in hydrocarbon conversion processes that have traditionally used a dual-function catalyst. In a narrower aspect, the present invention comprehends the improved hydrocarbon conversion processes that are produced by the use under carefully controlled environmental conditions of a catalytic composite comprising a combination of catalytically effective amounts of a platinum group component, a cobalt component, a tin component, and a halogen component with a porous carrier material; specifically, an improved reforming process which utilizes the subject catalyst and environmental conditions to improve activity, selectivity, and stability characteristics.

Composites having a hydrogenation-dehydrogenation function and a carbonium ion-forming function are widely used today as catalysts in many industries, such as the petroleum and petrochemical industry, to accelerate a wide spectrum of hydrocarbon conversion reactions. Generally, the carbonium ion-forming function is thought to be associated with an acid-acting material of the porous, adsorptive, refractory oxide type which is typically utilized as the support or carrier for a heavy metal component such as the metals or compounds of metals of Groups V through VIII of the Periodic Table to which are generally attributed the hydrogenation-dehydrogenation function.

These catalytic composites are used to accelerate a wide variety of hydrocarbon conversion reactions such as hydrocracking, hydrogenolysis, isomerization, dehydrogenation, hydrogenation, desulfurization, cyclization, polymerization, alkylation, cracking, hydroisomerization, dealkylation, transalkylation, etc. In many cases, the commercial applications of these catalysts are in processes where more than one of the reactions are proceeding simultaneously. An example of this type of process is reforming wherein a hydrocarbon feed-stream containing paraffins and naphthenes is subjected to conditions which promote dehydrogenation of naphthenes to aromatics, dehydrocyclization of paraffins to aromatics, isomerization of paraffins and naphthenes, hydrocracking and hydrogenolysis of naphthenes and paraffins and the like reactions, to produce an octane-rich or aromatic-rich product stream. Another example is a hydrocracking process wherein catalysts of this type are utilized to effect selective hydrogenation and cracking of high molecular weight unsaturated materials, selective hydrocracking of high molecular weight materials, and other like reactions, to produce a generally lower boiling, more valuable output stream. Yet another example is a hydroisomerization process wherein a hydrocarbon fraction which is relatively rich in straight-chain paraffin compounds is contacted with a dual-function catalyst to produce an output stream rich in isoparaffin compounds.

Regardless of the reaction involved or the particular process involved, it is of critical importance that the dual-function catalyst exhibit not only the capability to initially perform its specified functions, but also that it has the capability to perform them satisfactorily for prolonged periods of time. The analytical terms used in the art to measure how well a particular catalyst performs its intended functions in a particular hydrocarbon reaction environment are activity, selectivity, and stability. And for purposes of discussion here, these terms are conveniently defined for a given charge stock as follows: (1) activity is a measure of the catalyst's ability to convert hydrocarbon reactants into products at a specified severity level where severity level means the conditions used—that is, the temperature, pressure, contact time, and presence of diluents such as $H_2$; (2) selectivity refers to the amount of desired product or products obtained relative to the amount of reactants charged or converted; (3) stability refers to the rate of change with time of the activity and selectivity parameters—obviously, the smaller rate implying the more stable catalyst. In a reforming process, for example, activity commonly refers to the amount of conversion that takes place for a given charge stock at a specified severity level and is typically measured by octane number of the $C_5+$ product stream; selectivity refers to the amount of $C_5+$ yield relative to the amount of the charge that is obtained at the particular activity or severity level; and stability is typically equated to the rate of change with time of activity, as measured by octane number of $C_5+$ product, and of selectivity as measured by $C_5+$ yield. Actually, the last statement is not strictly correct because generally a continuous reforming process is run to produce a constant octane $C_5+$ product with severity level being continuously adjusted to attain this result; and furthermore, the severity level is for this process usually varied by adjusting the conversion temperature in the reaction zone so that, in point of fact, the rate of change of activity finds response in the rate of change of conversion temperatures and changes in this last parameter are customarily taken as indicative of activity stability.

As is well known to those skilled in the art, the principal cause of observed deactivation or instability of a dual-function catalyst when it is used in a hydrocarbon conversion reaction is associated with the fact that coke forms on the surface of the catalyst during the course of the reaction. More specifically, in these hydrocarbon conversion processes, the conditions utilized typically result in the formation of heavy, high molecular weight, black, solid or semi-solid, carbonaceous material which is a hydrogen-deficient polymeric substance having properties akin to both polynuclear aromatics and graphite. This material coats the surface of the catalyst and thus reduces its activity by shielding its active sites from the reactants. In other words, the performance of this dual-function catalyst is sensitive to the presence of carbonaceous deposits or coke on the surface of the catalyst. Accordingly, the major problem facing workers in this area of the art is the development of more active and/or selective catalytic composites that are not as sensitive to the presence of these carbonaceous materials and/or have the capability to suppress the rate of the formation of these carbonaceous materials on the catalyst. Viewed in terms of performance parameters, the problem is to develop a dual-function catalyst having superior activity, selectivity, and stability characteristics. In particular, for a reforming process the problem is typically expressed in terms of shifting and stabilizing the $C_5+$ yield-octane relationship at the lowest possible severity level—$C_5+$ yield being representative of selectivity and octane being proportional to activity.

In our prior application we disclosed a dual-function acidic multimetallic catalytic composite which possesses improved activity, selectivity, and stability characteristics when it is employed in a process for the conversion of hydrocarbons of the type which have heretofore utilized dual-function acidic catalytic composites such as processes for isomerization, hydroisomerization, dehydrogenation, desulfurization, denitrogenization, hydrogenation, alkylation, dealkylation, disproportionation, polymerization, hydrodealkylation, transalkylation, cyclization, dehydrocyclization, cracking, hydrocracking, halogenation, reforming, and the like processes. In particular, we have previously reported that an acidic catalyst, comprising a combination of catalytically effective amounts of a platinum group component, a cobalt component, a tin component, and a halogen component with a porous refractory carrier material, can enable the performance of hydrocarbon conversion processes utilizing dual-function catalysts to be substantially improved if the metallic components are uniformly dispersed throughout the carrier material and if their oxidation states are controlled to be in the states hereinafter specified. Now we have found that hydrocarbon conversion processes using our previously disclosed dual-function acidic multimetallic catalytic composite can be substantially further improved if this catalyst is used in a reaction zone which is maintained substantially free of detrimental sulfur and water contaminants through the judicious use of at least one guard bed to remove debilitating amounts of sulfur and water contaminants which are not ordinarily removed from feed streams to hydrocarbon conversion processes by conventional hydrorefining or hydrodesulfurization pretreatments. Viewed in terms of catalyst performance, our present invention essentially involves recognition that the multimetallic catalyst disclosed in our prior application is extraordinarily sensitive to the presence of trace amounts of sulfur and water contaminants when it is used in hydrocarbon conversion service; and a substantial further improvement in its catalytic performance is, quite surprisingly, achieved if it is used in a reaction zone which is operated under superclean conditions insofar as sulfur and water contaminants are concerned. Without the intention of being limited by this explanation, it is believed that the acute sensitivity to trace amounts of sulfur and water contaminants, which are not ordinarily removed from hydrocarbon charge stocks in a conventional pretreatment operation such as hydrodesulfurization, hydrorefining, and the like high temperature hydrogen treating processes, is attributable to the apparent ability of these contaminants to convert a portion of the catalytically available cobalt component from the catalytically effective elemental metallic state to the catalytically ineffective oxide or sulfide state, thereby causing the performance of the instant catalyst to fall short of its intrinsic potential. Even more significantly, we have ascertained that the degradation in performance associated with these contaminants is cumulative and is not reversible by conventional reactivation techniques and that it, therefore, appears to be permanent. Fortunately, we have now established that conventional sulfur- and water-selective adsorbents, when properly applied to the input streams used with the instant catalyst, are capable of obviating this hypersensitivity problem. In sum then, the present invention essentially involves coupling the acidic multimetallic catalyst disclosed in our prior application with a superclean reaction environment in order to enable a further significant improvement in hydrocarbon conversion processes of the type which have traditionally used a dual-function catalyst.

It is, accordingly, a principal object of the present invention to provide means whereby the acute sulfur and water sensitivity of the acidic multimetallic catalyst disclosed in our prior application is prevented from interfering with the achievement of its full potential for catalyzing the conversion of hydrocarbons. In other words, the objective of the present invention is to further improve the performance of the subject catalyst in a hydrocarbon conversion process by eliminating a major mode of catalyst deactivation which we have discovered for this catalyst In brief summary, one embodiment of the present invention is a process for converting a hydrocarbon charge stock which comprises contacting the hydrocarbon charge stock and a hydrogen stream at hydrocarbon conversion conditions, in a reaction zone maintained in a substantially sulfur- and water-free condition, with an acidic catalytic composite comprising a porous carrier material containing, on an elemental basis, about 0.01 to about 2 wt. % platinum group metal, about 0.5 to about 5 wt. % cobalt, about 0.01 to about 5 wt. % tin, and about 0.1 to about 3.5 wt. % halogen, wherein the platinum group metal, catalytically available cobalt, and tin are uniformly dispersed throughout the porous carrier material, wherein substantially all of the platinum group metal is present in the elemental metallic state, wherein substantially all of the tin is present in an oxidation state above that of the elemental metal, and wherein substantially all of the catalytically available cobalt is present in the elemental metalllic state or in a state which is reducible to the elemental metallic state under hydrocarbon conversion conditions or in a mixture of these states.

A second embodiment involves a process as described in the first embodiment wherein the sulfur- and water-free condition is achieved and maintained by treating the hydrocarbon charge stock, prior to passage of same into the reaction zone, with a first guard bed containing a sulfur- and water-selective adsorbent at first adsorption conditions effective to produce a treated charge stock containing less than 1 wt. ppm. sulfur and less than 1 wt. ppm. of water, and by treating the hydrogen stream, prior to passage of same into the reaction zone, with a second guard bed containing a sulfur- and water-selective adsorbent at second adsorption conditions effective to form a treated hydrogen stream containing less than 1 vol. ppm. of sulfur and less than 1 vol. ppm. of water.

A third embodiment involves a process as outlined in the first embodiment wherein substantially all of the hydrogen stream is obtained by recycling a portion of the effluent from the reaction zone and wherein the sulfur- and water-free condition is achieved and maintained by treating the hydrocarbon charge stock, prior to passage of same into the reaction zone, with a guard bed containing a sulfur- and water-selective adsorbent at adsorption conditions effective to produce a treated charge stock containing less than 1 wt. ppm. of sulfur and less than 1 wt. ppm. of water.

Another embodiment involves a process as defined in the first embodiment wherein a mixture of the hydrocarbon charge stock and the hydrogen stream is formed outside of the reaction zone and the mixture is thereafter passed into the reaction zone and wherein the sulfur- and water-free condition is achieved and maintained by treating the mixture with a guard bed containing a sulfur- and water-selective adsorbent at adsorption conditions effective to produce a treated mixture containing less than 1 wt. ppm. of sulfur and less than 1 wt. ppm. of water.

Other objects and embodiments are hereinafter given in the following detailed discussion of the principal features of the present invention.

As used herein the expression "catalytically available cobalt" is intended to mean the portion of the cobalt component that is available for use in accelerating the particular hydrocarbon conversion reaction of interest. For certain types of carrier materials which can be used in the preparation of the instant catalyst composite, it has been observed that a portion of the cobalt incorporated therein is essentially bound-up in the crystal structure thereof in a manner which essentially makes it more a part of the refractory carrier material than a catalytically active component. Specific examples of this effect are observed when the carrier material can form a spinel or spinel-like structure with a portion of the cobalt component. When this effect occurs, it is only with great difficulty that the portion of the cobalt bound-up with the support can be reduced to a catalytically active state and the conditions required to do this are beyond the severity levels normally associated with hydrocarbon conversion conditions and are in fact likely to seriously damage the necessary porous characteristics of the support. In the cases where cobalt can interact with the crystal structure of the support to render a portion thereof catalytically unavailable, the concept of the present invention merely requires that the amount of cobalt added to the subject catalyst be adjusted to satisfy the requirements of the support as well as the catalytically available cobalt requirements of the present invention. Against this background then, the hereinafter stated specifications for oxidation state and dispersion of the cobalt component are to be interpreted as directed to a description of the catalytically available cobalt. On the other hand, the specifications for the amount used are to be interpreted to include all of the cobalt contained in the catalyst in any form.

The acidic multimetallic catalyst used in the improved process of the present invention comprises a porous carrier material or support having combined therewith catalytically effective amounts of a platinum group component, a cobalt component, a tin component, and a halogen component.

Considering first the porous carrier material utilized in the present invention, it is preferred that the material be a porous, adsorptive, high-surface area support having a surface area of about 25 to about 500 m$^2$/g. The porous carrier material should be relatively refractory to the conditions utilized in the hydrocarbon conversion process and it is intended to include within the scope of the present invention carrier materials which have traditionally been utilized in dual-function hydrocarbon conversion catalysts such as: (1) activated carbon, coke, or charcoal; (2) silica or silica gel, silicon carbide, clays and silicates including those synthetically prepared and naturally occurring, which may or may not be acid treated, for example, attapulgus clay, china clay, diatomaceous earth, fuller's earth, kaoline, kieselguhr, etc., (3) ceramics, porcelain, crushed firebrick, bauxite; (4) refractory inorganic oxides such as alumina, titanium dioxide, zirconium dioxide, chromium oxide, beryllium oxide, vanadium oxide, cesium oxide, hafnium oxide, zinc oxide, magnesia, boria, thoria, silica-alumina, silica-magnesia, chromia-alumina, alumina-boria, silica-zirconia, etc.; (5) crystalline zeolitic aluminosilicates, such as naturally occurring or synthetically prepared mordenite and/or faujasite, either in the hydrogen form or in a form which has been treated with multivalent cations; (6) spinels such as $MgAl_2O_4$, $FeAl_2O_4$, $ZnAl_2O_4$, $MnAl_2O_4$, $CaAl_2O_4$, and other like compounds having the formula $MO \cdot Al_2O_3$ where M is a metal having a velence of 2; and, (7) combinations of elements from one or more of these groups. The preferred porous carrier materials for use in the present invention are refractory inorganic oxides, with best results obtained with an alumina carrier material. Suitable alumina materials are the crystalline aluminas known as gamma-, eta-, and theta-alumina, with gamma- or eta-alumina giving best results. In addition, in some embodiments the alumina carrier material may contain minor proportions of other well known refractory inorganic oxides such as silica, zirconia, magnesia, etc.; however, the preferred support is substantially pure gamma- or eta-alumina. Preferred carrier materials have an apparent bulk density of about 0.3 to about 0.8 g/cc and surface area characteristics such that the average pore diameter is about 20 to 300 Angstroms, the pore volume is about 0.1 to about 1 cc/g and the surface area is about 100 to about 500 m$^2$/g. In general, best results are typically obtained with a gamma-alumina carrier material which is used in the form of spherical particles having: a relatively small diameter (i.e. typically about 1/16 inch), an apparent bulk density of about 0.3 to about 0.8 g/cc, a pore volume of about 0.4 cc/g and a surface area of about 150 to about 250 m$^2$/g.

The preferred alumina carrier material may be prepared in any suitable manner and may be synthetically prepared or natural occurring. Whatever type of alumina is employed, it may be activated prior to use by one or more treatments including drying, calcination, steaming, etc., and it may be in a form known as activated alumina, activated alumina of commerce, porous alumina, alumina gel, etc. For example, the alumina carrier may be prepared by adding a suitable alkaline reagent, such as ammonium hydroxide, to a salt of aluminum such as aluminum chloride, aluminum nitrate, etc., in an amount to form an aluminum hydroxide gel which upon drying and calcining is converted to alumina. The alumina carrier may be formed in any desired shape such as spheres, pills, cakes, extrudates, powders, granules, tablets, etc., and utilized in any desired size. For the purpose of the present invention a particularly preferred form of alumina is the sphere; and alumina spheres may be continuously manufactured by the well known oil drop method which comprises: forming an alumina hydrosol by any of the techniques taught in the art and preferably by reacting aluminum metal with hydrochloric acid, combining the resultant hydrosol with a suitable gelling agent and dropping the resultant mixture into an oil bath maintained at elevated temperatures. The droplets of the mixture remain in the oil bath until they set and form hydrogel spheres. The spheres are then continuously withdrawn from the oil bath and typically subjected to specific aging treatments in oil and an ammoniacal solution to further improve their physical characteristics. The resulting aged and gelled particles are then washed and dried at a relatively low temperature of about 300° F. to about 400° F. and subjected to a calcination procedure at a temperature of about 850° F. to about 1300° F. for a period of about 1 to about 20 hours. This treatment effects conversion of the alumina hydrogel to the corresponding crystalline gamma-alumina. See the teachings of U.S. Pat. No. 2,620,314 for additional details.

One constituent of the acidic multimetallic composite used in the present invention is a tin component, and it is an essential feature of the present invention that substantially all of the tin component in the composite is in an oxidation state above that of the elemental metal. That is, it is believed that best results are obtained when substantially all of the tin component exists in the catalytic composite in the +2 or +4 oxidation state. Accordingly, the tin component will be present in the composite as a chemical compound such as the oxide, halide, oxyhalide, and the like, wherein the tin moiety is in a positive oxidation state, or in chemical combination with the carrier material in a manner such that the tin component is in a positive oxidation state. Controlled reduction experiments with the catalytic composites produced by the preferred methods of preparing the instant catalytic composite have established that the tin component in these catalysts is in a positive oxidation state and is not reduced by contact with hydrogen at temperatures in the range of 1000° to 1200° F. It is important to note that this limitation on the oxidation state of the tin component requires extreme care in preparation and use of the present catalyst to insure that it is not subjected to a reducing atmosphere at temperatures above 1200° F. Equally significant is the observation that it is only when the tin component is in a uniformly dispersed state in the carrier material that it has the capability to maintain its positive oxidation state when subjected to hereinafter described prereduction step. Stated another way, if the tin component is not properly dispersed on the support it can be reduced in the prereduction step and result in an inferior catalyst. Based on the evidence currently available it is believed that best results are obtained when the tin component is present in the catalyst as tin oxide. The term "tin oxide" as used herein refers to a coordinated tin-oxygen complex which is not necessarily stoichiometric.

Interrelated with this oxidation state limitation are the factors of dispersion of the tin component in the support and of particle size of the tin component. It has been established that it is only when the tin component is uniformly dispersed throughout the carrier material in a particle or crystallite size having a maximum dimension less than 100 Angstroms that is can successfully maintain its preferred oxidation state when it is subjected to a high temperature prereduction treatment or to hydrocarbon conversion conditions as hereinafter described. Thus it is an essential feature of our invention that the instant acidic multimetallic catalytic composite is prepared in a manner selected to meet the stated particle size and uniform dispersion limitations. By the use of the expression "uniform dispersion of a specified component in the carrier material" it is intended to describe the situation where the concentration of the specified ingredient is approximately the same in any reasonably divisable portion of the carrier material. Similarly, the expression "particles or crystallites having a maximum dimension less than 100 Angstroms" is intended to denote particles that would pass through a sieve having a 100 Angstrom mesh size if it were possible to make such a sieve.

The tin component may be incorporated into the catalytic composite in any suitable manner known to effectively disperse this component throughout the carrier material in the required particle size. Thus this component may be added to the carrier by coprecipitation or cogellation of a suitable soluble tin salt with the carrier material, by ion-exchange of suitable tin ions with ions contained in the carrier material when the ion exchange sites are uniformly distributed throughout the carrier or controlled impregnation of the carrier material with a suitable soluble tin salt under conditions selected to result in penetration of all sections of the carrier material by the tin component. One preferred method of incorporating the tin component involves coprecipitating or cogelling it during the preparation of the preferred carrier material, alumina. This method typically involves the addition of a suitable soluble tin compound such as stannous or stannic chloride to an alumina hydrosol, mixing these ingredients to obtain a uniform distritution of the tin moiety throughout the sol and then combining the hydrosol with a suitable gelling agent and dropping the resulting mixture into an oil bath etc., as explained in detail hereinbefore. After drying and calcining the resulting gelled carrier material there is obtained an intimate combination of alumina and tin oxide having the required dispersion and particle size. Another preferred method of incorporating the tin component into the catalytic composite involves utilization of a soluble, decomposable compound of tin to impregnate the porous carrier material. In general, the solvent used in this impregnation step is selected on the basis of the capability to dissolve the desired tin compound and to hold the tin moiety in solution until it is evenly distributed throughout the carrier material and is preferably an aqueous, rather strongly acidic solution. Thus the tin component may be added to the carrier material by commingling the latter with an aqueous solution of a suitable tin salt or suitable compound of tin such as stannous bromide, stannous chloride, stannic chloride, stannic chloride pentahydrate, stannic chloride diamine, stannic trichloride bromide, stannic chromate, stannous fluoride, stannic fluoride, stannic iodide, stannic sulfate, stannic tartrate, and the like compounds. The acid used in the impregnation solution may be any organic or inorganic acid that is capable of maintaining the pH of the impregnation solution in the range of about −1 or less to about 3 and preferably less than 1 during the impregnation step and that does not contaminate the resultant catalyst. Suitable acids are: inorganic acids such as hydrochloric acid, nitric acid, and the like; and strongly acidic organic acids such as oxalic acid, malonic acid, citric acid, malic acid, formic acid, tartaric acid, and the like. A particularly preferred impregnation solution comprises stannic or stannous chloride dissolved in a hydrochloric acid solution containing HCl in an amount corresponding to at least about 5 wt. % of the carrier material which is to be impregnated. Another useful impregnation solution is stannous or stannic chloride dissolved in an anhydrous alcohol such as ethanol. In general, the tin component can be incorporated either prior to, simultaneously with, or after the other metallic components are added to the carrier material. However, we have found that excellent results are obtained when the tin component is incorporated in the carrier material during its preparation and the other metallic components are added in a subsequent impregnation step after the tin-containing carrier material is calcined.

Regarding the amount of the tin component contained in the instant composite, it is preferably sufficient to constitute about 0.01 to about 5 wt. % of the final composite, calculated on an elemental basis, although substantially higher amounts of tin may be utilized in some cases. Best results are typically obtained with about 0.1 to about 2 wt. % tin.

A second essential ingredient of the subject catalyst is the platinum group component. That is, it is intended to cover the use of platinum, iridium, osmium, ruthenium, rhodium, palladium, or mixtures thereof as a second component of the present composite. It is an essential feature of the present invention that substantially all of this platinum group component exists within the final catalytic composite in the elemental metallic state. Generally, the amount of this component present in the final catalytic composite is small compared to the quantities of the other components combined therewith. In fact, the platinum group component generally will comprise about 0.01 to about 2 wt. % of the final catalytic composite, calculated on an elemental basis. Excellent results are obtained when the catalyst contains about 0.05 to about 1 wt. % of the platinum, iridium, rhodium, or palladium metal. Particularly preferred mixtures of these metals are platinum and iridium and platinum and rhodium.

This platinum group component may be incorporated in the catalytic composite in any suitable manner known to result in a relatively uniform distribution of this component in the carrier material such as coprecipitation or cogellation, ion exchange, or impregnation. The preferred method of preparing the catalyst involves the utilization of a soluble, decomposable compound of platinum group metal to impregnate the carrier material in a relatively uniform manner. For example, this component may be added to the support by commingling the latter with an aqueous solution of chloroplatinic or chloroiridic or chloropalladic acid. Other water-soluble compounds or complexes of platinum groups metals may be employed in impregnation solutions and include ammonium chloroplatinate, bromoplatinic acid, platinum trichloride, platinum tetrachloride hydrate, platinum dichlorocarbonyl dichloride, dinitrodiaminoplatinium, sodium tetranitroplatinate (II), palladium chloride, palladium nitrate, palladium sulfate, diamminepalladium (II) hydroxide, tetramminepalladium (II) chloride, hexamminerhodium chloride, rhodium carbonylchloride, rhodium trichloride hydrate, rhodium nitrate, sodium hexachlororhodate (III), sodium hexanitrorhodate (III), iridium tribromide, iridium dichloride, iridium tetrachloride, sodium hexanitroiridate (III), potassium or sodium chloroiridate, potassium rhodium oxalate, etc. The utilization of a platinum, iridium, rhodium, or palladium chloride compound, such as chloroplatinic, chloroiridic, or chloropalladic acid or rhodium trichloride hydrate, is preferred since it facilitates the incorporation of both the platinum group components and at least a minor quantity of the halogen component in a single step. Hydrogen chloride or the like acid is also generally added to the impregnation solution in order to further facilitate the incorporation of the halogen component and the uniform distribution of the metallic components throughout the carrier material. In addition, it is generally preferred to impregnate the carrier material after it has been calcined in order to minimize the risk of washing away the valuable platinum or palladium compounds; however, in some cases it may be advantageous to impregnate the carrier material when it is in a gelled state.

A third essential ingredient of the acidic multimetallic catalytic composite of the present invention is a cobalt component. Although this component may be initially incorporated into the composite in many different decomposable forms which are hereinafter stated, our basic finding is that the catalytically active state for hydrocarbon conversion with this component is the elemental metallic state. Consequently, it is a feature of our invention that substantially all of the catalytically available cobalt component exists in the catalytic composite either in the elemental metallic state or in a state which is reducible to the elemental state under hydrocarbon conversion conditions or in a mixture of these states. Examples of this last state are obtained when the catalytically available cobalt component is initially present in the form of cobalt oxide, hydroxide, halide, oxyhalide, and the like reducible compounds. As a corollary to this basic finding on the active state of the catalytically available cobalt component, it follows that the presence of the catalytically available cobalt in forms which are not reducible at hydrocarbon conversion conditions is to be scrupulously avoided if the full benefits of the present invention are to be realized. Illustrative of these undesired forms are cobalt sulfide and the cobalt oxysulfur compounds such as cobalt sulfate. Best results are obtained when the composite initially contains all of the catalytically available cobalt component in the elemental metallic state or in a reducible oxide state or in a mixture of these states. All available evidence indicates that the preferred preparation procedure specifically described in Example I results in a catalyst having the catalytically available cobalt component in a reducible oxide form. The cobalt component may be utilized in the composite in any amount which is catalytically effective, with the preferred amount being about 0.5 to about 5 wt. % thereof, calculated on an elemental cobalt basis. Typically, best results are obtained with about 0.5 to about 2 wt. % cobalt. It is, additionally, preferred to select the specific amount of cobalt from within this broad weight range as a function of the amount of the platinum group component, on an atomic basis, as is explained hereinafter.

The cobalt component may be incorporated into the catalytic composite in any suitable manner known to those skilled in the catalyst formulation art to result in a relatively uniform distribution of the catalytically available cobalt in the carrier material such as coprecipitation, cogellation, ion exchange, impregnation, etc. In addition, it may be added at any stage of the preparation of the composite—either during preparation of the carrier material or thereafter—since the precise method of incorporation used is not deemed to be critical. However, best results are obtained when the catalytically available cobalt component is relatively uniformly distributed throughout the carrier material in a relatively small particle or crystalline size having a maximum dimension of less than 100 Angstroms, and the preferred procedures are the ones that are known to result in a composite having a relatively uniform distribution of the catalytically available cobalt moiety in a relatively small particle size. One acceptable procedure for incorporating this component into the composite involves cogelling or coprecipitating the cobalt component during the preparation of the preferred carrier material, alumina. This procedure usually comprehends the addition of a soluble, decomposable, and reducible compound of cobalt such as cobalt chloride or nitrate to the alumina hydrosol before it is gelled. The resulting mixture is then finished by conventional gelling, aging, drying, and calcination steps as explained hereinbefore. One preferred way of incorporating this component is an impregnation step wherein the porous carrier material is impregnated with a suitable cobalt-containing solution either before, during, or after the carrier material is calcined or oxidized. The solvent used to form the impregnation solution may be water, alcohol, ether, or any other suitable organic or inorganic solvent provided the solvent does not adversely interact with any of the other ingredients of the composite or interfere with the distribution and reduction of the cobalt component. Preferred impregnation solutions are aqueous solutions of water-soluble, decomposable, and reducible cobalt compounds such as cobaltous acetate, cobaltous benzoate, cobaltous bromate, cobaltous bromide, cobaltous chlorate and perchlorate, cobaltous chloride, cobaltic chloride, cobaltous fluoride, cobaltous iodide, cobaltous nitrate, hexamminecobalt (III) chloride, hexamminecobalt (III) nitrate, triethylenediamminecobalt (III) chloride, cobaltous hexamethylenetetramine, and the like compounds. Best results are ordinarily obtained when the impregnation solution is an aqueous solution of cobalt chloride or cobalt nitrate. This cobalt component can be added to the carrier material, either prior to, simultaneously with, or after the other metallic components are combined therewith. Best results are usually achieved when this component is added simultaneously with the platinum group component via an acidic aqueous impregnation solution. In fact, excellent results are obtained, as reported in the examples, with an impregnation procedure using an acidic aqueous solution comprising chloroplatinic acid, cobaltous chloride, and hydrochloric acid.

It is essential to incorporate a halogen component into the acidic multimetallic catalytic composite used in the present invention. Although the precise form of the chemistry of the association of the halogen component with the carrier material is not entirely known, it is customary in the art to refer to the halogen component as being combined with the carrier material, or with the other ingredients of the catalyst in the form of the halide (e.g. as the chloride). This combined halogen may be either fluorine, chlorine, iodine, bromine, or mixtures thereof. Of these, fluorine and particularly chlorine are preferred for the purposes of the present invention. The halogen may be added to the carrier material in any suitable manner, either during preparation of the support or before or after the addition of the other components. For example, the halogen may be added, at any stage of the preparation of the carrier material or to the calcined carrier material, as an aqueous solution of a suitable, decomposable halogen-containing compound such as hydrogen fluoride, hydrogen chloride, hydrogen bromide, ammonium chloride, etc. The halogen component or a portion thereof, may be combined with the carrier material during the impregnation of the latter with the platinum group, cobalt, or tin components; for example, through the utilization of a mixture of chloroplatinic acid and hydrogen chloride. In another situation, the alumina hydrosol which is typically utilized to form the preferred alumina carrier material may contain halogen and thus contribute at least a portion of the halogen component to the final composite. For reforming, the halogen will be typically combined with the carrier material in an amount sufficient to result in a final composite that contains about 0.1 to about 3.5%, and preferably about 0.5 to about 1.5%, by weight of halogen, calculated on an elemental basis. In isomerization or hydrocracking embodiments, it is generally preferred to utilize relatively larger amounts of halogen in the catalyst—typically ranging up to about 10 wt. % halogen calculated on an elemental basis, and more preferably, about 1 to about 5 wt. %. It is to be understood that the specified level of halogen component in the instant catalyst can be achieved or maintained during use in the conversion of hydrocarbons by continuously or periodically adding to the reaction zone a decomposable halogen-containing compound such as an organic chloride (e.g. ethylene dichloride, carbon tetrachloride, t-butyl chloride) in an amount of about 1 to 100 wt. ppm. of the hydrocabon feed, and preferably about 1 to 10 wt. ppm.

Regarding especially preferred amounts of the various metallic components of the subject catalyst, we have found it to be a good practice to specify the amounts of the cobalt component and the tin component as a function of the amount of the platinum group component. On this basis, the amount of the cobalt component is ordinarily selected so that the atomic ratio of cobalt to platinum group metal contained in the composite is about 0.8:1 to about 66:1, with the preferred range being about 1.6:1 to about 18:1. Similarly, the amount of the tin component is ordinarily selected to produce a composite containing an atomic ratio of tin to platinum or palladium metal of about 0.1:1 to about 13:1, with the preferred range being about 0.3:1 to about 5:1.

Another significant parameter for the instant catalyst is the "total metals content" which is defined to be the sum of the platinum group component, the cobalt component, and the tin component, calculated on an elemental basis. Good results are ordinarily obtained with the subject catalyst when this parameter is fixed at a value of about 0.15 to about 4 wt. % with best results ordinarily achieved at a metals loading of about 0.3 to about 3 wt. %.

In embodiments of the present invention wherein the instant multimetallic catalytic composite is used for the dehydrogenation of dehydrogenatable hydrocarbons or for the hydrogenation of hydrogenatable hydrocarbons, it is ordinarily a preferred practice to minimize or eliminate the halogen component and to include an alkali or alkaline earth metal component in the composite. More precisely, this optional ingredient is selected from the group consisting of the compounds of the alkali metals—cesium, rubidium, potassium, sodium, and lithium—and the compounds of the alkaline earth metals—calcium, strontium, barium, and magnesium. Generally, good results are obtained in these embodiments when this component constitutes about 0.1 to about 5 wt. % of the composite, calculated on an elemental basis. This optional alkali or alkaline earth metal component can be incorporated in the composite in any of the known ways, with impregnation with an aqueous solution of a suitable water-soluble, decomposable compound being preferred.

An optional ingredient for the multimetallic catalyst used in the present invention is a Friedel-Crafts metal halide component. This ingredient is particularly useful in hydrocarbon conversion embodiments of the present invention wherein it is preferred that the catalyst utilized has a strong acid or cracking function associated therewith—for example, an embodiment wherein hydrocarbons are to be hydrocracked or isomerized with the catalyst of the present invention. Suitable metal halides of the Friedel-Crafts type include aluminum chloride, aluminum bromide, ferric chloride, ferric bromide, zinc chloride, and the like compounds, with the aluminum halides and particularly aluminum chloride ordinarily yielding best results. Generally, this optional ingredient can be incorporated into the composite of the present invention by any of the conventional methods for adding metallic halides of this type; however, best results are ordinarily obtained when the metallic halide is sublimed onto the surface of the carrier material according to the preferred method disclosed in U.S. Pat. No. 2,999,074. The component can generally be utilized in any amount which is catalytically effective, with a value selected from the range of about 1 to about 100 wt. % of the carrier material generally being preferred.

Regardless of the details of how the components of the catalyst are combined with the porous carrier material, the final catalyst generally will be dried at a temperature of about 200° to about 600° F. for a period of at least about 2 to about 24 hours or more, and finally calcined or oxidized at a temperature of about 700° F. to about 1100° F. in an air or oxygen atmosphere for a period of about 0.5 to about 10 hours in order to convert substantially all of the metallic components to the corresponding oxide form. Because a halogen component is utilized in the catalyst, best results are generally obtained when the halogen content of the catalyst is adjusted during the oxidation step by including a halogen or a halogen-containing compound such as HCl in the air or oxygen atmosphere utilized. In particular, when the halogen component of the catalyst is chlorine, it is preferred to use a mole ratio of $H_2O$ to HCl to about 5:1 to about 100:1 during at least a portion of the oxidation step in order to adjust the final chlorine content of the catalyst to a range of about 0.1 to about 3.5 wt. %. Preferably, the duration of this halogenation step is about 1 to 5 hours.

The resultant oxidized catalytic composite is preferably subjected to a substantially water-free and hydrocarbon-free reduction step prior to its use in the conversion of hydrocarbons. This step is designed to selectively reduce the platinum group component to the elemental metallic state and to insure a uniform and finely divided dispersion of the metallic components throughout the carrier material, while maintaining the tin component in a positive oxidation state. Preferably substantially pure and dry hydrogen (i.e. less than 20 vol. ppm. $H_2O$) is used as the reducing agent in this step. The reducing agent is contacted with the oxidized catalyst at conditions including a reduction temperature of about 800° F. to about 1200° F. and a period of time of about 0.5 to 10 hours effective to reduce substantially all of the platinum group component to the elemental metallic state while maintaining the tin component in an oxidation state above that of the elemental metal. Quite surprisingly, we have found that if this reduction step is performed with a hydrocarbon-free hydrogen stream at the temperature indicated and if the catalytically available cobalt component is properly distributed in the carrier material in the oxide form and in the specified particle size, no substantial amount of the catalytically available cobalt component will be reduced in this step. However, once the catalyst sees a mixture of hydrogen and hydrocarbon, substantially all of the catalytically available cobalt component is quickly reduced at the specified reduction temperature range. This reduction treatment may be performed in situ as part of a start-up sequence if precautions are taken to predry the plant to a substantially water-free state and if substantially water-free and hydrocarbon-free hydrogen is used.

The resulting reduced catalytic composite is, in accordance with the basic concept of the present invention, maintained in a sulfur-free state both during its preparation and thereafter during its use in the conversion of hydrocarbons. As indicated previously, the beneficial interaction of the cobalt component with the other ingredients of the present catalytic composite is contingent upon the maintenance of the catalytically available cobalt moiety in a highly dispersed, readily reducible state in the carrier material. Sulfur in the form of sulfide adversely interfers with both the dispersion and reducibility of the cobalt component and consequently it is essential to avoid presulfiding the selectivity reduced acidic multimetallic catalyst resulting from the reduction step.

According to the present invention, a hydrocarbon charge stock and a hydrogen stream are contacted with the instant acidic multimetallic catalyst in a hydrocarbon conversion zone maintained in a substantially sulfur-free and water-free condition. This contacting may be accomplished by using the catalyst in a fixed bed system, a moving bed system, a fluidized bed system, or in a batch type operation; however, in view of the danger of attrition losses of the valuable catalyst and of well known operational advantages, it is preferred to use either a fixed bed system or a dense-phase moving bed system such as is shown in U.S. Pat. No. 3,725,249. It is also contemplated that this contacting step can be performed in the presence of a physical mixture of particles of the catalyst of the present invention and particles of a conventional dual-function catalyst of the prior art. In a fixed bed system, a hydrogen-rich gas and the charge stock are preheated by any suitable heating means to the desired reaction temperature and then are passed into a conversion zone containing a fixed bed of the acidic multimetallic catalyst. It is, of course, understood that the conversion zone may be one or more separate reactors with suitable means therebetween to insure that the desired conversion temperature is maintained at the entrance to each reactor. It is also important to note that the reactants may be contacted with the catalyst bed in either upward, downward, or radial flow fashion with the latter being preferred. In addition, the reactants may be in the liquid phase, a mixed liquid-vapor phase, or a vapor phase when they contact the catalyst, with best results obtained in the vapor phase.

In the case where the acidic multimetallic catalyst used in the present invention is used in a reforming operation, the reforming system will typically comprise a reforming zone containing one or more fixed beds or dense-phase moving beds of the catalyst. In a multiple bed system, it is, of course, within the scope of the present invention to use the present catalyst in less than all of the beds with a conventional dual-function catalyst being used in the remainder. This reforming zone may be one or more separate reactors with suitable heating means therebetween to compensate for the endothermic nature of the reactions that take place in each catalyst bed. The hydrocarbon feed stream that is charged to this reforming system will comprise hydrocarbon fractions containing naphthenes and paraffins that boil within the gasoline range. The preferred charge stocks are those consisting essentially of naphthenes and paraffins, although in some cases aromatics and/or olefins may also be present. This preferred class includes straight run gasolines, natural gasolines, synthetic gasolines, partially reformed gasolines, and the like. On the other hand, it is frequently advantageous to charge thermally or catalytically cracked gasolines or higher boiling fractions thereof. Mixtures of straight run and cracked gasoline can also be used to advantage. The gasoline charge stock may be a full boiling gasoline having an initial boiling point of from about 50° to about 150° F. and an end boiling point within the range of from about 325° to about 425° F., or may be a selected fraction thereof which generally will be a higher boiling fraction commonly referred to as a heavy naphtha—for example, a naphtha boiling in the range of $C_7$ to 400° F. In some cases, it is also advantageous to charge pure hydrocarbons or mixtures of hydrocarbons that have been extracted from hydrocarbon distillates—for example, straight-chain paraffins—which are to be converted to aromatics.

In other hydrocarbons conversion embodiments, the charge stock will be of the conventional type customarily used for the particular kind of hydrocarbon conversion being effected. For example, in a typical isomerization embodiment the charge stock can be a paraffinic stock rich in $C_4$ to $C_8$ normal paraffins, or a normal butane-rich stock, or a n-hexanerich stock, or a mixture of xylene isomers, or an olefin-rich stock, etc. In a dehydrogenation embodiment, the charge stock can be any of the known dehydrogenatable hydrocarbons such as an aliphatic compound containing 2 to 30 carbon atoms per molecule, a $C_4$ to $C_{30}$ normal paraffins a $C_8$ to $C_{12}$ alkylaromatic, a naphthene, and the like. In hydrocracking embodiments, the charge stock will be typically a gas oil, heavy cracked cycle oil, etc. In addition, alkylaromatics, olefins, and naphthenes can be conveniently isomerized by using the catalyst of the present invention. Likewise, pure hydrocarbons or substantially pure hydrocarbons can be converted to more valuable products by using the acidic multimetallic catalyst of the present invention in any of the hydrocarbon conversion processes, known to the art, that use a dual-function catalyst.

A key feature of the present invention is the use of the instant catalyst in a reaction zone which is continuously maintained in a substantially sulfur- and water-free condition. The expression "substantially sulfur- and water-free condition" is intended to mean; 1) that the total amount of sulfur contaminants in any form (such as elemental sulfur, hydrogen sulfide, sulfur-containing organic or inorganic compounds) entering the reaction zone, calculated on the basis of elemental sulfur, from any source is continuously maintained at a value corresponding to less than 1 wt. ppm. of the hydrocarbon charge stock passed thereto, and 2) that the total amount of water or water-producing contaminants (such as oxygen and oxygen-containing organic and inorganic compounds) entering the reaction zone, calculated on the basis of equivalent water, is continuously maintained at a value corresponding to less than 1 wt. ppm. of the hydrocarbon charge stock passed thereto. This stringent requirement for a superclean environment is to be maintained throughout the duration of the hydrocarbon conversion run once the instant catalyst is started-up and lined-out at hydrocarbon conversion conditions. During the start-up period, some deviation from the stated condition is tolerable insofar as the water-free part of the requirement is concerned; however, the sulfur-free restriction must be met even during the start-up period in order to realize the full benefits of the present invention.

The sources for the sulfur and water contaminants of concern here in the type of hydrocarbon conversion process contemplated by the present invention are: the hydrocarbon charge stock, the hydrogen stream, the catalyst and the hydrocarbon conversion plant hardware. Of these, the principal source is the hydrocarbon charge stock with the other sources only becoming of major significance in the special circumstances considered hereinafter.

Since all of the hydrocarbon charge stock contemplated for use in the present process will contain amounts of sulfur and water contaminants substantially above the amounts previously specified, it is necessary to pretreat the charge stock for contaminant removal. In the case where the levels of these contaminants is not more than a factor of about ten to about 100 above the specified value, the charge stock can be directly treated in the subsequently described contaminant adsorption step. In the more typical case where these contaminants are present in gross amounts ranging up to 1 wt. % or more of the hydrocarbon charge stock, the concept of the present invention requires a two-step treatment operation consisting of a first gross contaminant removal step followed by the contaminant adsorption step.

The gross contaminant removal step ordinarily involves a relatively high temperature catalytic treatment of the charge stock with hydrogen such as hydrorefining, hydrotreating, hydrodesulfurization, and the like to remove the major portion of sulfurous, nitrogenous, and water-yielding contaminants from this feedstream. Ordinarily, this involves subjecting the sulfur and water contaminant-containing feedstream to contact with a suitable sulfur-resistant hydrorefining catalyst in the presence of hydrogen under conversion conditions selected to decompose sulfur, nitrogen, and oxygen contaminants contained therein and to form hydrogen sulfide, water, and ammonia. The hydrorefining catalyst typically comprises one or more of the oxides or sulfides of the transition metals of Groups VI or VIII of the Periodic Table. A particularly preferred hydrorefining catalyst comprises a combination of a metallic component from the iron group metals of Group VIII and of a metallic component of the Group VI transition metals combined with a suitable porous refractory support. Particularly good results have been obtained when the iron group component is cobalt and/or nickel and the Group VI transition metal is molybdenum or tungsten. The preferred support for this type of catalyst is a refractory inorganic oxide of the type previously mentioned. For example, good results are obtained with a hydrorefining catalyst comprising cobalt oxide and molybdenum oxide supported on a carrier material comprising alumina and silica. The conditions utilized in this hydrorefining step are ordinarily selected from the following ranges: a temperature of about 600° to about 950° F., a pressure of about 500 to about 5000 psig., a liquid hourly space velocity of about 1 to about 20 hr. $^{-1}$, and a hydrogen circulation rate of about 500 to about 10,000 standard cubic feet of hydrogen per barrel of charge. After this hydrorefining step, a substantial portion of the hydrogen sulfide, ammonia, and water liberated therein, are easily removed from the resulting purified charge stock by conventional means such as a suitable stripping operation. Specific hydrorefining conditions are selected from the ranges given above as a function of the amounts and kinds of the sulfur, oxygen, and nitrogen contaminants in the feedstream in order to produce a partially treated charge stock which is then charged to the contaminant adsorption step of the present invention. It is to be noted that under certain circumstances with a relatively easily treatable charge stock, it may be possible to achieve the specified sulfur and water contents for the present invention in this hydrogen treating step without resorting to a subsequent contaminant adsorption step; however, this mode of operation is definitely not preferred because of the substantial danger of an upset in the hydrogen treating step causing inadvertent release of the detrimetal contaminants into the reaction zone containing the instant catalyst, with consequential inevitable damage thereto.

The contaminant adsorption step operates on the partially treated stream from the hydrogen treating step or directly on the hydrocarbon charge when gross removal of contaminants is not necessary as previously explained. The primary function performed by this contaminant adsorption step is removal of trace amount of the sulfur and water contaminants which are either not economically removable by conventional hydrogen treating methods of which are relatively intractable under hydrorefining conditions or which are not completely removed in the stripping step which follows the hydrogen treating step. Even when the charge stock to the adsorption step is within the specified superclean specification, it is preferred to treat it in the adsorption step in order to guard against upsets in upstream equipment caused by charge stock variations, operator error, power failure, etc. This last possibility is the reason why this adsorption step is performed in a zone which is identified herein as a "guard bed".

According to the present invention, the hydrocarbon charge stock is contacted with a sulfur- and water-selective adsorbent at adsorption conditions effective to produce a fully treated charge stock containing less than 1 wt. ppm. of sulfur and less than 1 wt. ppm. of water. This adsorption step is performed just prior to the introduction of the charge stock into the hydrocarbon conversion step of the present process, and in general, involves passing the charge stock through a guard bed containing the adsorbent as a dense compact fixed or moving bed, with a fixed bed operation being preferred. The particle size of the adsorbent is generally selected to effect good contact between the charge stock and same, without causing excessive pressure drop across the bed, and is generally about 5 to about 100 U.S. Mesh.

The adsorbent used in the guard bed can be any suitable adsorbent known to those skilled in the adsorption art which can remove all of the remaining sulfur and water contaminants from the charge stock. In general, it is selected from the following categories: (1) high surface area particles of a reactive metal, (2) high surface area particles of a sulfuraccepting reactive metal oxide, (3) sulfur- and water-selective clay or clay-like material, (4) in the special case where the sulfur and water contaminants are limited to $H_2S$ and $H_2O$, by partially dehydrated crystalline zeolitic aluminosilicates having substantially uniform pores between about 4 to about 13 Angstroms in diameter, and (5) mixtures of these adsorbents.

The reactive metals suitable for use as adsorbents are potassium, sodium, magnesium, aluminum, zinc, copper, iron, nickel, cobalt and the like electropositive metals which in finely divided form have a high affinity for sulfur and water contaminants. In addition, mixture of metals can be utilized. The reactive metals can be used in the form of shaving, filings, powders, or they can be supported on a suitable porous carrier material such as activated alumina, porous clays, silica, bauxite, and the like.

The reactive metal oxides which can be used are those which have a propensity for accepting sulfur and forming the corresponding metal sulfide. Suitable metals oxide are alumina, zinc oxide, copper oxide, magnesium oxide, iron oxide, cobalt oxide, nickel oxide, manganese oxide, and the like sulfur-accepting reactive metal oxide. Mixtures of these metal oxides are also contemplated. Since generally these metal oxides form water when they adsorb sulfur contaminants and since they may have a low selectivity for water contaminants, it is preferred to use them in combination with a suitable desiccant. The desiccant may be utilized in admixture with the metal or the bed of the metal oxide particles can be followed by a bed of desiccant particles or the metal oxide can be supported on an carrier material having desiccant properties such as dehydrated crystalline zeolitic aluminosilicates, activated alumina, silica gel, bauxite, calcium chloride impregnated alumina, magnesium oxide, and the like materials. The sulfur-accepting metal oxide can be used in the form of spheres, powders, pills, pellets, or the like or it can be supported on a suitable porous carrier material as in the case of the reactive metal.

Adsorptive clays can be used as the adsorbent when the sulfur and water contaminants are relatively tractable. Suitable sulfur- and water-selective clays are fuller's earth, attapulgite, kaolin, hectorite, montmorillonite, and the like material which may be activated prior to use by a suitable acid treatment if desired.

Considering all of the above-mentioned adsorbents, we have found best results when the guard bed comprises finely divided particles of high surface area sodium. It is, of course, to be understood that the adsorbent can either be utilized until its adsorbent power is exhausted and then discarded or it can be regenerated in certain cases by methods known to those skilled in the art such by treatment with hydrogen at high temperatures.

The adsorption conditions used are selected on the basis of the characteristics of the adsorbent and the charge stock to effet the specified degree of contaminant removal. Generally, temperatures of about 0 to 800° F. and pressure of about atmospheric to 500 psig. are used. Contact time may range from about 0.1 to about 100 minutes depending on the particular circumstances. Generally, the pressure and temperature used are the minimum required for the degree of decontamination required. Likewise, the adsorption step can be carried out under liquid or a vapor phase condition, with a liquid phase operation being preferred for the highly reactive metal adsorbents and a vapor phase operation for the rest. When a vapor phase operation is used, the adsorption pressure and temperature are preferably quite close to those used in the hydrocarbon conversion step.

A second possible source of sulfur and water contaminants is the hydrogen stream passed to the reaction zone. In general, the hydrogen stream can be treated, prior to passage of same into the reaction zone, by a guard bed containing a sulfur- and water-selective adsorbent at adsorption conditions effective to form a treated hydrogen stream containing less than 1 vol. ppm. of sulfur and less than 1 vol. ppm. of water. Since the contaminants present in the hydrogen stream are predominately $H_2O$ and $H_2S$, this is a relatively easier job than treating the charge stock; nevertheless; all of the adsorbents previously discussed can be utilized for this operation. The adsorption conditions used in this hydrogen treating step are selected in the manner previously indicated for the charge stock treating step.

In general, it is preferred to separately treat the hydrogen stream and the hydrocarbon charge stock with different beds of adsorbents which can be tailored for the particular characteristics of each. However, in one mode of operation it is possible to use only one guard bed with a mixture of the hydrogen stream and the hydrocarbon charge stock being treated therein prior to passage of the mixture into the reaction zone. In the special case wherein substantially all of the hydrogen stream is autogenously produced in the hydrocarbon conversion step and recycled to the reaction zone (i.e. net hydrogen production occurs in the reaction zone) then a mode of operation can be used wherein, after the process is started-up and lined-out, only the hydrocarbon charge need be treated for contaminant removal in the manner previously indicated since the hydrogen stream will inherently be free of the undesired contaminants when the charge stock is properly treated. For example, in the ordinary operation of a conventional catalytic reforming process, wherein influent hydrogen is autogenously produced, the prime source for any sulfur or water contaminants entering the reforming zone is the hydrocarbon charge stock. Maintaining the charge stock substantially free of sulfur and water contaminants is ordinarily sufficient to ensure that the environment containing the catalyst is maintained in the substantially surfur-free and water-free state. More specifically, since hydrogen is a by-product of the catalytic reforming process, ordinarily the input hydrogen stream required for the process is obtained by recycling a portion of the hydrogen-rich stream recovered from the effluent withdrawn from the reforming zone. In this typical situation, the recycle hydrogen stream will ordinarily be substantially free of sulfur and water contaminants if the charge stock is maintained free of sulfur and water contaminants.

The only other possible sources of sulfur and water contaminants that could interfere with the performance of the instant catalyst are contaminants that are initially combined with the catalyst and/or with the plant hardware. As indicated hereinbefore, an essential feature of the present acidic multimetallic catalyst is that it is maintained substantially sulfur-free; therefore, sulfur released from the catalyst is not usually a problem in the present process. Water released from the catalyst during start-up can be controlled by a guard bed used on the recycle hydrogen stream as previously explained and also by drying the plant and catalyst out prior to feed cut-in with a suitable drying gas stream. Hardware sulfur is ordinarily not present in a new plant; it only becomes a problem when the present process is to be implemented in a plant that has seen service with a sulfur-containing feedstream. In this latter case, the preferred practice of the present invention involves an initial pretreatment of the sulfur-containing plant in order to remove substantially all of the decomposable hardware sulfur therefrom. This can be easily accomplished by any of the techniques for stripping sulfur from hardware known to those in the art; for example, by the circulation of a substantially sulfur-free hydrogen stream through the internals of the plant at a relatively high temperature of about 800° to about 1200° F. until the $H_2S$ content of the effluent gas stream drops to a relatively low level—typically, less than 5 vol. ppm. and preferably less than 2 vol. ppm.

The conditions utilized in the numerous hydrocarbon conversion embodiments of the present invention are in general those customarily used in the art for the particular reaction, or combination of reactions that is to be effected. For instance, alkylaromatic, olefin, and paraffin isomerization conditions include: a temperature of about 32° F. to about 1000° F. and preferably from about 75° to about 600° F.; a pressure of atmospheric to about 100 atmospheres; a hydrogen to hydrocarbon mole ratio of about 0.5:1 to about 20:1 and an LHSV (calculated on the basis of equivalent liquid volume of the charge stock contacted with the catalyst per hour divided by the volume of conversion zone containing catalyst) of about 0.2 hr.$^{-1}$ to 10 hr.$^{-1}$. Dehydrogenation conditions include: a temperature of about 700° to about 1250° F., a pressure of about 0.1 to about 10 atmospheres, a liquid hourly space velocity of about 1 to 40 hr.$^{-1}$, and a hydrogen to hydrocarbon mole ratio of about 1:1 to 20:1. Likewise, typically hydrocracking conditions include: a pressure of about 500 psig. to about 3000 psig., a temperature of about 400° F. to about 900° F., an LHSV of about 0.1 hr.$^{-1}$ to about 10 hr.$^{-1}$, and hydrogen circulation rates of about 1000 to 10,000 SCF per barrel of charge.

In the reforming embodiment of the present invention, the pressure utilized is selected from the range of about 0 psig. to about 1000 psig., with the preferred pressure being about 50 psig. to about 600 psig. Particularly good results are obtained at low or moderate pressure; namely, a pressure of about 100 to 450 psig. In fact, it is a singular advantage of the present invention that it allows stable operation at lower pressures than have heretofore been successfully utilized in so-called "continuous" reforming systems (i.e. reforming for periods of about 15 to about 200 or more barrels of charge per pound of catalyst without regeneration) with all platinum monometallic catalyst. In other words, the acidic multimetallic catalyst of the present invention allows the operation of a continuous reforming system to be conducted at lower pressure (i.e. 100 to about 350 psig.) for about the same or better catalyst cycle life before regeneration as has been heretofore realized with conventional monometallic catalysts at higher pressure (i.e. 400 to 600 psig.). On the other hand, the extraordinary activity and activity-stability characteristics of the catalyst of the present invention enables reforming conditions conducted at pressures of 400 to 600 psig. to achieve substantially increased catalyst cycle life before regeneration.

The temperatures required for reforming with the instant catalyst is markedly lower than that required for a similar reforming operation using a high quality catalyst of the prior art. This significant and desirable feature of the present invention is a consequence of the extraordinary activity of the acidic multimetallic catalyst of the present invention for the octane-upgrading reactions that are preferably induced in a typical reforming operation. Hence, the present invention requires a temperature in the range of from about 800° F. to about 1100° F. and preferably about 900° F. to about 1050° F. As is well known to those skilled in the continuous reforming art, the initial selection of the temperature within this broad range is made primarily as a function of the desired octane of the product reformate considering the characteristics of the charge stock and of the catalyst. Ordinarily, the temperature then is thereafter slowly increased during the run to compensate for the inevitable deactivation that occurs to provide a constant octane product. Therefore, it is a feature of the present invention that not only is the initial temperature requirement substantially lower but also the rate at which the temperature is increased in order to main a constant octane product is substantially lower for the catalyst of the present invention than for an equivalent operation with a high quality reforming catalyst which is manufactured in exactly the same manner as the catalyst of the present invention except for the inclusion of the cobalt and tin components. Moreover, for the catalyst of the present invention, the $C_5+$ yield loss for a given temperature increase is substantially lower than for a high quality reforming catalyst of the prior art. The extraordinary activity of the instant catalyst can be utilized in a number of highly beneficial ways to enable increases performance of a catalytic reforming process relative to that obtained in a similar operation with a monometallic or bimetallic catalyst of the prior art, some of these are: (1) octane number of $C_5+$ product can be substantially increased without sacrificing catalyst run length. (2) the duration of the process operation (i.e. catalyst run length or cycle life) before regeneration becomes necessary can be significantly increased. (3) $C_5+$ yield can be increased by lowering average reactor pressure with no change in catalyst run length. (4) investment costs can be lowered without any sacrifice in cycle life by lowering recycle gas requirements thereby saving on capital cost for compressor capacity or by lowering initial catalyst loading requirements thereby saving on cost of catalyst and on capital cost of the reactors. (5 throughput can be increased sharply at no sacrifice in catalyst cycle life if sufficient heater capacity is available.

The reforming embodiment of the present invention also typically utilizes sufficient hydrogen to provide an amount of about 1 to about 20 moles of hydrogen per mole of hydrocarbon entering the reforming zone, with excellent results being obtained when about 2 to about 6 moles of hydrogen are used per mole of hydrocarbon. Likewise, the liquid hourly space velocity (LHSV) used in reforming is selected from the range of about 0.1 to about 10 hr.$^{-1}$, with a value in the range of about 1 to about 5 hr.$^{-1}$ being preferred. In fact, it is a feature of the present invention that it allows operations to be conducted at higher LHSV than normally can be stably achieved in a continuous reforming process with a high quality reforming catalyst of the prior art. This last feature is of immense economic significance because it allows a continuous reforming process to operate at the same throughput level with less catalyst inventory or at greatly increased throughput level with the same catalyst inventory than that heretofore used with conventional reforming catalysts at no sacrifice in catalyst cycle life before regeneration.

The following examples are given to illustrate further the preparation of the acidic multimetallic catalytic composite used in the present invention and the improvement associated with the use thereof in the conversion of the hydrocarbons in a reaction zone maintained in a substantially sulfur-free and water-free condition. It is understood that the examples are intended to be illustrative rather than restrictive.

EXAMPLE I

A tin-containing, sulfur-free alumina carrier material comprising 1/16 inch spheres was prepared by: forming an aluminum hydroxyl chloride sol by dissolving substantially pure aluminum pellets in a hydrochloric acid solution, adding stannic chloride to the resulting sol in an amount selected to result in a finished catalyst containing about 0.2 wt. % tin, adding hexamethylenetetramine to the resulting tin-containing alumina sol, gelling the resulting solution by dropping it into an oil bath to form spherical particles of an aluminum- and tin-containing hydrogel, aging and washing the resulting particles and finally drying and calcining the aged and washed particles to form spherical particles of gamma-alumina containing a uniform dispersion of about 0.2 wt. % tin in the form of tin oxide and about 0.3 wt. % combined chloride. Additional details as to this method of preparing the preferred gamma-alumina carrier material are given in the teachings of U.S. Pat. No. 2,620,314.

A sulfur-free aqueous impregnation solution containing chloroplatinic acid, cobaltous chloride, and hydrogen chloride was then prepared. The tin-containing alumina carrier material was thereafter admixed with the impregnation solution. The amount of reagents contained in this impregnation solution was calculated to result in a final composite containing, on an elemental basis, 0.30 wt. % platinum and 1.0 wt. % cobalt. In order to insure uniform dispersion of the metallic components throughout the carrier material, the amount of hydrochloric acid used was about 3 wt. % of the alumina particles. This impregnation step was performed by adding the carrier material particles to the impregnation mixture with constant agitation. In addition, the volume of the solution was approximately the same as the void volume of the carrier material particles. The impregnation mixture was maintained in contact with the carrier material particles for a period of about ½ to about 3 hours at a temperature of about 70° F. Thereafter, the temperature of the impregnation mixture was raised to about 225° F. and the excess solution was evaporated in a period of about 1 hour. The resulting dried impregnation particles were then subjected to an oxidation treatment in a dry sulfur-free air stream at a temperature of about 975° F. and a GHSV of about 500 hr.$^{-1}$ for about ½ hour. This oxidation step was designed to convert substantially all of the metallic ingredients to the corresponding oxide forms. The resulting oxidized spheres were subsequently contacted in a halogen treating step with a sulfur-free air stream containing $H_2O$ and HCl in a mole ratio of about 30:1 for about 2 hours at 975° F. and a GHSV of about 500 hr.$^{-1}$ in order to adjust the halogen content of the catalyst particles to a value of about 1.12 wt. %. The halogen-treated spheres were thereafter subjected to a second oxidation step with a dry air stream at 975° F. and a GHSV of 500 hr.$^{-1}$ for an additional period of about ½ hour.

The resulting oxidized and halogen treated catalyst particles were then subjected to a dry prereduction treatment, designed to reduce the platinum component to the elemental state while maintaining the tin component in positive oxidation state, by contacting them for about 1 hour with a substantially hydrocarbon-free and sulfur-free dry hydrogen stream containing less than 5 vol. ppm. $H_2O$ at a temperature of about 1050° F., a pressure slightly above atmospheric, and a flow rate of the hydrogen stream through the catalyst particles corresponding to a gas hourly space velocity of about 400 hr.$^{-1}$.

Examination of a sample of the resulting reduced catalyst by gas adsorption and controlled reduction techniques indicated that substantially all of the platinum component had been reduced whereas substantially all of the tin component remained in the tin oxide state. Likewise controlled reduction experiments along with additional evidence from electron spin resonance established that at the completion of this reduction step, substantially all of the catalytically available cobalt component was in a readily reducible oxide form. X-ray and electron spin resonance studies of the cobalt crystallites contained in the instant catalyst after it had been exposed to hydrocarbons during the subsequently described reforming operation indicated that substantially all of the catalytically available cobalt component was reduced to the elemental metallic state at the reforming conditions utilized.

A sample of the resulting reduced catalyst particles was analyzed and found to contain, on an elemental basis, about 0.30 wt. % platinum, about 1.0 wt. % cobalt, about 0.2 wt. % tin, and about 1.12 wt. % chloride. This corresponds to an atomic ratio of tin to platinum of 1.1:1 to an atomic ratio of cobalt to platinum of 11:1.

EXAMPLE II

In order to demonstrate the improvement associated with the superclean environment requirement of the present invention, two separate hydrocarbon conversion test runs were performed with separate portions of the catalyst prepared in Example I. In the first test run only conventional hydrorefining was used to clean-up the charge stock. In the second test run a guard bed containing finely divided particles of high surface area sodium was used to further treat the hydrorefined charge stock in order to remove trace quantities of sulfur and water contaminants as required by the present invention. In all other respects, the two tests were performed at identical conditions.

The hydrocarbon conversion test used for comparison was a high stress accelerated catalytic reforming test designed to determine in a relatively short period of time the relative activity, selectivity, and stability characteristics of the catalyst in the different environments. In both test runs the same charge stock was utilized and its pertinent characteristics are set forth in Table I. As noted above, in the second test run the charge stock was treated in a guard bed containing a high surface area sodium adsorbent at conditions selected to remove substantially all of the sulfur and water contaminants therefrom. This treatment step was performed under liquid phase conditions and prior to passage of the charge stock into the reaction zone containing the catalyst.

TABLE I

| Analysis of Charge Stock | |
|---|---|
| Gravity, ° API at 60° F. | 59.1 |
| Distillation Profile, ° F. | 202 |
| Initial Boiling Point | 218 |
| 5% Boiling Point | 226 |
| 10% Boiling Point | 250 |
| 30% Boiling Point | 266 |
| 50% Boiling Point | 296 |
| 70% Boiling Point | 322 |
| 90% Boiling Point | 334 |
| 95% Boiling Point | 382 |
| Nitrogen, wt. ppm. | 0.1 |
| Sulfur, wt. ppm. | 0.2 |
| Water, wt. ppm. | 14 – 18 |
| Octane Number, F-1 clear | 37.6 |
| Paraffins, vol. % | 68.85 |
| Naphthenes, vol. % | 21.72 |
| Aromatics, vol. % | 9.02 |

This accelerated reforming test was specifically designed to determine in a very short period of time whether the catalyst and environment being evaluated has superior characteristics for use in a high severity reforming operation. Each run consisted of a series of evaluation periods of 24 hours, each of these periods comprised a 12 hour line-out period followed by a 12 hour test period during which the $C_5+$ product reformate from the plant was collected and analyzed. Both test runs were performed at identical conditions which comprised a liquid hourly space velocity (LHSV) of 3.0 hr.$^{-1}$, a pressure of 300 psig., a 10:1 gas to oil ratio, and an inlet reactor temperature which was continuously adjusted throughout the test in order to achieve and maintain a $C_5+$ target octane of 100 F-1 clear.

Both tests were performed in a pilot plane scale reforming unit comprising a reaction zone containing a fixed bed of the catalyst undergoing evaluation, a hydrogen separation zone, a debutanizer column, and suitable heating means, pumping means, condensing means, compressing means, and the like conventional equipment. The flow scheme utilized in this plant involves commingling a hydrogen recycle stream with the charge stock and heating the resulting mixture to the desired conversion temperature. The heated mixture is then passed downflow into a reactor containing catalyst undergoing evaluation as a stationary bed. An effluent stream is then withdrawn from the bottom of the reactor, cooled to about 55° F. and passed to a gas-liquid separation zone wherein a hydrogen-rich gaseous phase separates from a liquid hydrocarbon phase. A portion of the gaseous phase is then continuously passed through a high surface area sodium scrubber and the resulting substantially water-free and sulfur-free hydrogen stream is returned to the reactor in order to supply the hydrogen recycle stream. The excess gaseous phase from the separation zone is recovered as the hydrogen-containing product stream (commonly called "excess recycle gas"). The liquid phase from the separation zone is withdrawn therefrom and passed to a debutanizer column wherein light ends (i.e. $C_1$ to $C_4$) are taken overhead as debutanizer gas and a $C_5+$ reformate stream recovered as the principal bottom product.

The results of the separate tests performed with and without the charge stock guard bed are presented for each test period in Table II in terms of inlet temperature to the reactor in ° F. necessary to achieve the target octane level and the amount of $C_5+$ reformate recovered expressed as vol. % (LV%) of the charge stock.

TABLE II

Results of Accelerated Reforming Test

| Period | WITHOUT GUARD BED T, ° F | WITHOUT GUARD BED $C_5$+ LV% | WITH GUARD BED T, ° F | WITH GUARD BED $C_5$+ LV% |
|---|---|---|---|---|
| 1 | 960.5 | 68.48 | 957.0 | 69.02 |
| 2 | 966.0 | 70.25 | 950.0 | 70.40 |
| 3 | 973.0 | — | 953.0 | — |
| 4 | 979.5 | 72.11 | 951.0 | 70.71 |
| 5 | 984.0 | — | 955.5 | — |
| 6 | 988.5 | 73.19 | 955.5 | 70.61 |
| 7 | 992.0 | — | 957.0 | — |
| 8 | 1000.0 | 72.25 | 957.0 | 69.93 |
| 9 | — | — | 951.5 | — |
| 10 | — | — | 954.0 | 70.81 |
| 11 | — | — | 951.5 | — |
| 12 | — | — | 952.5 | 70.16 |
| 13 | — | — | 953.0 | — |

Referring now to the results of the comparison test presented in Table II, it is evident that the principal effect of the use of the charge stock guard bed is to enable a substantial improvement in the performance of the subject catalyst—especially in the areas of activity and activity-stability. As was pointed out in detail hereinbefore, a good measure of activity for a reforming catalyst is the inlet temperature in the reactor which is required to make target octane and the data presented in Table II on this variable clearly shows the catalyst with a feed guard bed was extraordinarily more active and stable than the catalyst without a feed guard bed. The average activity advantage that the present invention manifests is equal to or better than 25° F. in inlet reactor temperature and is truly outstanding when one realizes that, as a rule of thumb, the rate of a reaction ordinarily doubles for every 18° to 20° F. increase in reactor temperature. Thus, a 25° F. average activity advantage means that the process of the present invention is on the average approximately four or five times as active as the control process. A specific example of this activity advantage can be obtained by looking at the data for period 8 of the test (i.e. 192 hours into the test), at this point, the process of the present invention required an inlet temperature of 957.0° F. in order to make octane which stands in sharp contrast to the 1000.0° F. requirement of the control process at the same point in the run. This 43° F. difference in temperature requirement for octane is impressive evidence of the ability of the improved process of the present invention to materially accelerate the rate of the involved reforming reaction without materially changing the $C_5+$ yield. Thus, the data clearly shows that the process of the present invention was extraordinarily more active and stable than the control process.

It is intended to cover by the following claims, all changes and modifications of the above disclosure of the present invention which would be self-evident to a man of ordinary skill in the hydrocarbon conversion art or the catalyst formulation art.

We claim as our invention:

1. A process for converting a hydrocarbon charge stock which comprises contacting the hydrocarbon charge stock and a hydrogen stream at hydrocarbon conversion conditions, in a reaction zone maintained in a substantially sulfur- and water-free condition, with an acidic catalytic composite comprising a porous carrier material containing, on an elemental basis, about 0.01 to about 2 wt. % platinum group metal, about 0.5 to about 5 wt. % cobalt, about 0.01 to about 5 wt. % tin, and about 0.1 to about 3.5 wt. % halogen, wherein the platinum group metal, catalytically available cobalt, and tin are uniformly dispersed throughout the porous carrier material, wherein substantially all of the platinum group metal is present in the elemental metallic state, wherein substantially all of the tin is present in an oxidation state above that of the elemental metal wherein the average crystalline size of said tin is less than 100 Angstroms in maximum dimension, and wherein substantially all of the catalytically available cobalt is present in the elemental metallic state or in a state which is reducible to the elemental metallic under hydrocarbon conversion conditions or in a mixture of these states.

2. A process as defined in claim 1 wherein the sulfur- and water-free condition is achieved and maintained by treating the hydrocarbon charge stock, prior to passage of same into the reaction zone, with a first guard bed containing a sulfur- and water-selective adsorbent at first adsorption conditions effective to produce a treated charge stock containing less than 1 wt. ppm. sulfur and less than 1 wt. ppm. of water, and by treating the hydrogen stream, prior to passage of same into the reaction zone, with a second guard bed containing a sulfur- and water-selective adsorbent at second adsorption conditions effective to form a treated hydrogen stream containing less than 1 vol. ppm. of sulfur and less than 1 vol. ppm. of water.

3. A process as defined in claim 2 wherein at least one of said guard beds contains an adsorbent comprising high surface area particles of a reactive metal having a high affinity for water and sulfur.

4. A process as defined in claim 3 wherein the reactive metal is selected from the group consisting of potassium, sodium, magnesium, aluminum, zinc, iron, nickel, cobalt, copper, and mixtures thereof.

5. A process as defined in claim 2 wherein at least one of said guard beds contains an adsorbent comprising particles of a sulfur- and water-selective clay.

6. A process as defined in claim 2 wherein at least one of said guard beds comprises a mixture of particles of a sulfur-accepting reactive metal oxide and of a desiccant.

7. A process as defined in claim 2 wherein at least one of said guard beds comprises particles of a sulfur-accepting reactive metal oxide followed by particles of desiccant.

8. A process as defined in claim 6 wherein the sulfur-accepting reactive metal oxide is selected from the group consisting of alumina, zinc oxide, copper oxide, magnesium oxide, iron oxide, cobalt oxide, nickel oxide, and mixtures thereof.

9. A process as defined in claim 1 wherein substantially all of the hydrogen stream is obtained by recycling a portion of the effluent from the reaction zone and wherein the sulfur- and water-free condition is achieved and maintained by treating the hydrocarbon charge stock, prior to passage of same into the reaction zone, with a guard bed containing a sulfur- and water-selective adsorbent at adsorption conditions effective to produce a treated charge stock containing less than 1 wt. ppm. of sulfur and less than 1 wt. ppm. of water.

10. A process as defined in claim 9 wherein the adsorbent comprises high surface area particles of a reactive metal having a high affinity for water and sulfur.

11. A process as defined in claim 9 wherein the adsorbent comprises particles of a sulfur-accepting reactive metal oxide followed by particles of a desiccant.

12. A process as defined in claim 1 wherein a mixture of the hydrocarbon charge stock and the hydrogen stream is formed outside of the reaction zone and the mixture is thereafter passed into the reaction zone and wherein the sulfur- and water-free condition is achieved and maintained by treating the mixture with a guard bed containing a sulfur- and water-selective adsorbent at adsorption conditions effective to produce a treated mixture containing less than 1 wt. ppm. of sulfur and less than 1 wt. ppm. of water.

13. A process as defined in claim 1 wherein substantially all of the catalytically available cobalt contained in the composite is present in the elemental metallic state.

14. A process as defined in claim 1 wherein substantially all of the tin is present in the catalytic composite as tin oxide.

15. A process as defined in claim 1 wherein the composite contains about 0.05 to about 1 wt. % platinum, about 0.5 to about 2 wt. % cobalt, about 0.05 to about 1 wt. % tin, and about 0.5 to about 1.5 wt. % halogen.

16. A process as defined in claim 1 wherein the type of hydrocarbon conversion is catalytic reforming of a gasoline fraction to produce a high octane reformate, wherein the hydrocarbon is contained in the gasoline fraction, and wherein the hydrocarbon conversion conditions are reforming conditions.

17. A process as defined in claim 16 wherein the reforming conditions include a temperature of about 800° to about 1100° F., a pressure of about 0 to about 1000 psig., a liquid hourly space velocity of about 0.1 to about 10 hr.$^{-1}$, and a mole ratio of hydrogen to hydrocarbon of about 1:1 to about 20:1.

18. A process as defined in claim 16 wherein the reforming conditions include a pressure of about 100 to about 450 psig.

* * * * *